US00PP08720P

United States Patent [19]

Hill

[11] Patent Number: Plant 8,720

[45] Date of Patent: May 10, 1994

[54] APPLE TREE NAMED APPLEWAITES

[76] Inventor: Richard Hill, St. Andrew's Road, Havelock North, New Zealand

[21] Appl. No.: 936,821

[22] Filed: Aug. 28, 1992

[51] Int. Cl.[5] ..... A01H 5/00
[52] U.S. Cl. ..... Plt./34.1
[58] Field of Search ..... Plt. 34.1

[56] References Cited

PUBLICATIONS

Application for Plant Selectors' Rights and Protective Direction, Technical Questionnaire.
Objective Description of Variety Grant No. 610, Aug. 28, 1991.

*Primary Examiner*—James R. Feyrer
*Assistant Examiner*—E. F. McElwain
*Attorney, Agent, or Firm*—Quarles & Brady

[57] ABSTRACT

A new and distinct variety of apple tree designated Applewaites is a mutation of the Gala Variety and is characterized by an overall strong dark red colour.

1 Drawing Sheet

SUMMARY OF THE INVENTION

The present invention relates to a new and distinct apple variety. The new cultivar is designated 'Applewaites' and is a mutation of the Gala variety Kidds D8 (U.S. Plant Pat. No. 3,637).

After the variety was discovered in 1983 by the applicant in the Asparagus Limited Orchard, Hastings, New Zealand, it was asexually produced in 1984 at Limnos Investments property in Hastings, New Zealand by budding on to rootstock of the MM 106 variety. The fruit was first observed on the reproduced plants in 1986 at Asparagus Limited Orchard. Asexual propagation by budding shows that the unique combination of characteristics and distinctive colour come true to form and are established and transmitted through succeeding propagations.

BRIEF DESCRIPTION OF THE DRAWINGS

The accompanying photograph shows typical specimens of the fruit of the new variety as depicted in colours as nearly true as is reasonably possible to make the same in a colour illustration of this character.

DETAILED DESCRIPTION OF THE PLANT

Figure 1:
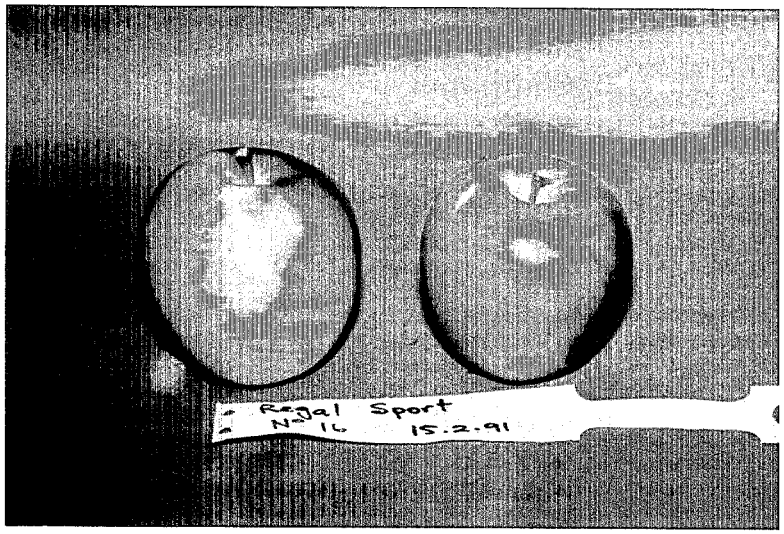
FIG. 1: shows both sides of the fruit, the overcolour and the background colour.

The distinctive characteristics of this new apple cultivar described below were observed in Hastings. The trees were three to six years old.

Applewaites is similar to Fulford (U.S. Plant Pat. No. 7,598) but has a more even red colouring deeper into the tree than Fulford. Colour development for Applewaites through the tree is superior to that achieved by Fulford. Applewaites has a strong bright red colouring over 70–90% of the fruit surface. In comparison to Fulford, Applewaites has a birghter more developed red colour over a greater proportion of the apple than Fulford. The harvest date for applewaites is on average, at the same location and management, earlier than Fulford. The open harvest dates for Applewaites ranged from February 5 to February 17 for the years 1986 through 1993. In comparison, the range of opening harvest dates over the same period for Fulford were 2–3 days later than those above. Under the same location and management, Applewaites is a weaker tree which sets a greater proportion of flowers than the Fulford variety. Applewaites is correspondingly more difficult than Fulford to thin with the standard accepted rates of chemical thinners. Fruit size for Applewaites is on average smaller as a result of the lower tree vigour and naturally higher fruit set than for Fulford. (Both Galaxy (U.S. Plant Pat. No. 6,955) and Treco Spur Red Gala No. 42 (U.S. Plant Pat. No. 7,396) have stripes showing underneath their red colour. Applewaites is a block red apple and has no stripe associated with the red colour development of the fruit. The colour of the Applewaites fruit is also distinctly different from the Galaxy fruit colour as indicated in the following colour measurements.

The colour designations hereinafter set forth are according to the Munsell Colour System using a Minolta colour meter.

Tree: Weak vigour; spreading habit; predominance of bearing on shoots.

Dormant one year old shoot (observed in winter on trees at least three years old): No pubescence on upper half; medium thickness; medium number of lenticels; dark brown colour on the sunny side; medium bud size; pointed bud tip; position of bud relative to axis; adpressed; small bud support; dormant fruit bud shape (on spurs), conical;

*Colour of laterals.*—Brown 5 GY 1/8–2.5 GY 2/11; pronounced white lenticels present.

Flower: colour of bud just before flower opens, pink; time of beginning of flowering (10% of flowers), medium; full bloom dates for the years 1986–1993 range from 5 October to 12 October. Petal colour of open flowers is 7.5RP7/3. The outside of the bud is a deep pink colour 7.5RP4/8.

*Observation of flowers at start of anther dehiscence.*—Flat or slightly cupped shape; large size (4.5–5.0 cm); position of margin of petals, free.

Leaf (Mature observed in summer when they form one thrid of an upright growing shoot on the outside of the tree): Early bud burst; pose of leaf, outwards, medium leaf size; from 4th to 6th fully expanded leaf, length 95 mm, width 49 mm; length/width ratio of blade, medium; shape in cross section, concave; indentation of margin, serrate; medium glossiness on upper side; weak pubescence on lower side; medium petiiole length, medium stipule size; colour of leaves from top of terminated laterals, green 7.5 GY 2/14–7.5 GY 1/7; leaves from growing lateral, lighter green 5 GY 3/21–5 GY 4/29.

Fruit:

Size.—Medium; length 66 mm, breadth 71 mm.

*Shape.*—Medium conical; symmetric in side view; weak crown at distal end.

*Eye.*—Closed; medium size.

*Eye basin.*—Medium depth; medium width; ribbing present.

*Sepals.*—Medium length; overlapping at base.

*Stalk.*—Thin; long.

*Stalk cavity.*—Deep; medium width.

*Skin.*—Ribbing present, not prominent; smooth surface; bloom, absent; greasiness, absent; cracking tendency, absent; medium skin thickness; green yellow ground colour - 10 YR 2/38–5Y 1/33.

*Overcolour.*—High percentage of overcolour - 70–90%; strong dark red 5R 10/45–2.5R 6/30; solid flush; low amount of russet around stalk.

*Lenticels.*—Medium size; noticeable on highly coloured areas of skin.

*Flesh.*—Firm; white-yellow 10 Y 3/21–10 Y 1/12; fine texture; juicy.

*Flavour.*—Medium sweetness; weak acidity.

*Calyx tube.*—Medium length; medium width; Y shaped.

*Sinus.*—Closed.

*Distinctiveness of core-line median through locules-.*—Weak when observed in cross section.

*Aperture of locules.*—Closed in cross-section.

*Central cavity.*—Absent in cross-section.

*Ripening.*—For eating, medium; 2 days later than Cox's Orange Pippen.

*Seed.*—Medium size; brown colour when dry, 5 GY 3/23.

I claim:

1. A new and distinct variety of apple which is a mutation of the Gala variety (U.S. Plant Pat. No. 3,637) substantially as shown and described, characterised by an overall strong dark red colour.

* * * * *